United States Patent
Mullin (10) Patent No.: US 11,857,420 B2
(45) Date of Patent: Jan. 2, 2024

(54) SACROILIAC JOINT FUSION IMPLANTS AND METHODS

(71) Applicant: Brad Mullin, New Albany, OH (US)

(72) Inventor: Brad Mullin, New Albany, OH (US)

(*) Notice: Subject to any disclaimer, the term of this patent is extended or adjusted under 35 U.S.C. 154(b) by 195 days.

(21) Appl. No.: 16/435,163

(22) Filed: Jun. 7, 2019

(65) Prior Publication Data
US 2020/0297496 A1 Sep. 24, 2020

Related U.S. Application Data

(60) Provisional application No. 62/820,345, filed on Mar. 19, 2019.

(51) Int. Cl.
*A61F 2/30* (2006.01)
*A61F 2/28* (2006.01)
*A61F 2/46* (2006.01)
*A61B 17/70* (2006.01)

(52) U.S. Cl.
CPC ........ *A61F 2/30988* (2013.01); *A61F 2/2846* (2013.01); *A61F 2/30749* (2013.01); *A61F 2/4603* (2013.01); *A61B 17/7011* (2013.01); *A61F 2002/3093* (2013.01); *A61F 2002/30622* (2013.01); *A61F 2002/30784* (2013.01); *A61F 2002/30995* (2013.01); *A61F 2310/00023* (2013.01)

(58) Field of Classification Search
CPC .. A61F 2002/30988; A61F 2002/30995; A61F 2/30749; A61F 2002/30736; A61F 2002/30754; A61F 2002/30766; A61F 2002/30769; A61F 2002/30622; A61B 17/7055
See application file for complete search history.

(56) References Cited

U.S. PATENT DOCUMENTS

| | | | | |
|---|---|---|---|---|
| D364,462 S | * | 11/1995 | Michelson | D24/145 |
| 5,607,424 A | | 3/1997 | Tropiano | |
| 5,683,391 A | * | 11/1997 | Boyd | A61F 2/4611 606/264 |
| 6,235,059 B1 | * | 5/2001 | Benezech | A61F 2/447 623/17.16 |
| 6,325,827 B1 | * | 12/2001 | Lin | A61B 17/025 623/17.16 |
| 7,837,732 B2 | * | 11/2010 | Zucherman | A61F 2/447 623/17.11 |
| 8,133,283 B2 | * | 3/2012 | Wilson | A61B 17/8061 623/21.14 |
| 8,337,532 B1 | * | 12/2012 | McLean | A61B 17/7032 606/279 |
| 10,194,962 B2 | * | 2/2019 | Schneider | A61B 17/84 |

(Continued)

FOREIGN PATENT DOCUMENTS

WO 2014/124453 A2 8/2014

*Primary Examiner* — Alvin J Stewart (74) *Attorney, Agent, or Firm* — Vorys, Sater, Seymour and Pease LLP (57) ABSTRACT

Presently disclosed is a sacroiliac joint implant. In an embodiment, a sacroiliac joint implant includes a porous body configured to promote bone growth. The porous body may have a window that is configured to hold a graft material. The porous body may also include a first face and second face configured to contact the sacrum and the ilium of the sacroiliac joint when the implant is maintained in compression within the sacroiliac joint.

21 Claims, 10 Drawing Sheets

(56) References Cited

U.S. PATENT DOCUMENTS

| | | | |
|---|---|---|---|
| 10,258,386 B2* | 4/2019 | Butler | A61B 17/7002 |
| 10,357,368 B2* | 7/2019 | Aksu | A61F 2/30 |
| 10,596,004 B2* | 3/2020 | Donner | A61F 2/30988 |
| 10,603,055 B2* | 3/2020 | Donner | A61B 17/1739 |
| 10,603,176 B2* | 3/2020 | Arnold | A61B 17/8066 |
| 2005/0149192 A1* | 7/2005 | Zucherman | A61B 17/1671 |
| | | | 623/17.11 |
| 2007/0106388 A1* | 5/2007 | Michelson | A61F 2/442 |
| | | | 623/17.16 |
| 2008/0021454 A1* | 1/2008 | Chao | A61B 17/7044 |
| | | | 606/250 |
| 2008/0021456 A1* | 1/2008 | Gupta | A61B 17/7049 |
| | | | 606/250 |
| 2008/0039843 A1* | 2/2008 | Abdou | A61B 17/7043 |
| | | | 606/255 |
| 2008/0154377 A1* | 6/2008 | Voellmicke | A61F 2/447 |
| | | | 623/17.16 |
| 2010/0004747 A1* | 1/2010 | Lin | A61B 17/7059 |
| | | | 623/17.16 |
| 2011/0106168 A1* | 5/2011 | Bucci | A61B 17/7032 |
| | | | 606/264 |
| 2011/0238181 A1* | 9/2011 | Trieu | A61B 17/1735 |
| | | | 623/17.11 |
| 2011/0264229 A1* | 10/2011 | Donner | A61F 2/30988 |
| | | | 623/18.11 |
| 2012/0083883 A1* | 4/2012 | Ginn | A61B 17/7074 |
| | | | 623/17.11 |
| 2012/0179205 A1* | 7/2012 | Miller | A61B 17/7041 |
| | | | 606/264 |
| 2012/0253398 A1* | 10/2012 | Metcalf | A61B 17/869 |
| | | | 606/264 |
| 2012/0296428 A1* | 11/2012 | Donner | A61F 2/30988 |
| | | | 623/17.11 |
| 2013/0123850 A1* | 5/2013 | Schoenefeld | A61B 17/7055 |
| | | | 606/248 |
| 2013/0144343 A1* | 6/2013 | Arnett | A61B 17/7055 |
| | | | 606/279 |
| 2013/0184760 A1* | 7/2013 | Ballard | A61B 17/7041 |
| | | | 606/278 |
| 2013/0304128 A1* | 11/2013 | Lange | A61B 17/7032 |
| | | | 606/264 |
| 2014/0031935 A1* | 1/2014 | Donner | A61B 17/7055 |
| | | | 623/17.11 |
| 2014/0088707 A1* | 3/2014 | Donner | A61B 17/0218 |
| | | | 623/17.11 |
| 2014/0135927 A1* | 5/2014 | Pavlov | A61B 17/7055 |
| | | | 623/17.11 |
| 2014/0200618 A1* | 7/2014 | Donner | A61F 2/4611 |
| | | | 606/281 |
| 2015/0112444 A1* | 4/2015 | Aksu | A61F 2/30 |
| | | | 623/18.11 |
| 2015/0173805 A1* | 6/2015 | Donner | A61F 2/46 |
| | | | 606/279 |
| 2015/0182268 A1* | 7/2015 | Donner | A61B 17/809 |
| | | | 606/281 |
| 2016/0081809 A1* | 3/2016 | Schneider | A61F 2/44 |
| | | | 623/17.11 |
| 2016/0081810 A1* | 3/2016 | Reiley | A61F 2/44 |
| | | | 623/17.11 |
| 2016/0106477 A1* | 4/2016 | Hynes | A61B 17/7032 |
| | | | 606/279 |
| 2016/0106479 A1* | 4/2016 | Hynes | A61B 17/7044 |
| | | | 606/286 |
| 2016/0310197 A1 | 10/2016 | Black et al. | |
| 2017/0245900 A1* | 8/2017 | Rezach | A61B 17/7035 |
| 2017/0296344 A1* | 10/2017 | Souza | A61B 17/68 |
| 2018/0014939 A1* | 1/2018 | Arnold | A61B 17/7059 |
| 2018/0110626 A1* | 4/2018 | McShane, III | A61F 2/447 |
| 2018/0228621 A1* | 8/2018 | Reiley | A61F 2/447 |
| 2018/0296347 A1* | 10/2018 | Hamzey | B33Y 80/00 |
| 2018/0360500 A1* | 12/2018 | Butler | A61B 17/705 |
| 2018/0360608 A1* | 12/2018 | Aksu | A61F 2/30 |
| 2019/0343640 A1* | 11/2019 | Donner | A61F 2/4405 |
| 2020/0146831 A1* | 5/2020 | Donner | A61B 17/8872 |
| 2020/0197050 A1* | 6/2020 | Ehteshami | A61B 17/7055 |
| 2020/0222088 A1* | 7/2020 | Kraus | A61B 17/7098 |
| 2020/0246158 A1* | 8/2020 | Bergey | A61F 2/447 |
| 2020/0261240 A1* | 8/2020 | Mesiwala | A61F 2/30907 |
| 2020/0268518 A1* | 8/2020 | Suh | A61F 2/4603 |
| 2020/0375630 A1* | 12/2020 | Kim | A61B 17/808 |
| 2021/0100662 A1* | 4/2021 | LaNeve | A61F 2/30988 |

* cited by examiner

SACROILIAC JOINT FUSION IMPLANTS AND METHODS

CROSS-REFERENCE TO RELATED APPLICATION

This application claims priority to and the benefit of U.S. Provisional Patent Application No. 62/820,345, filed Mar. 19, 2019, which is incorporated by reference herein in its entirety.

BACKGROUND OF THE INVENTION

The present disclosure relates to fusion surgery, and more particularly, to sacroiliac joint fusion.

The sacroiliac joint (the "SI joint") is a low-motion joint that connects the hip bones to either side of the sacrum, acting primarily as a shock-absorber between the lower body and torso. Dysfunction in the SI joint can produce significant lower back pain, as well as pelvic, groin, and hip pain. This dysfunction can be the result of too much motion, too little motion, or inflammation of the joint.

Figure 1A:
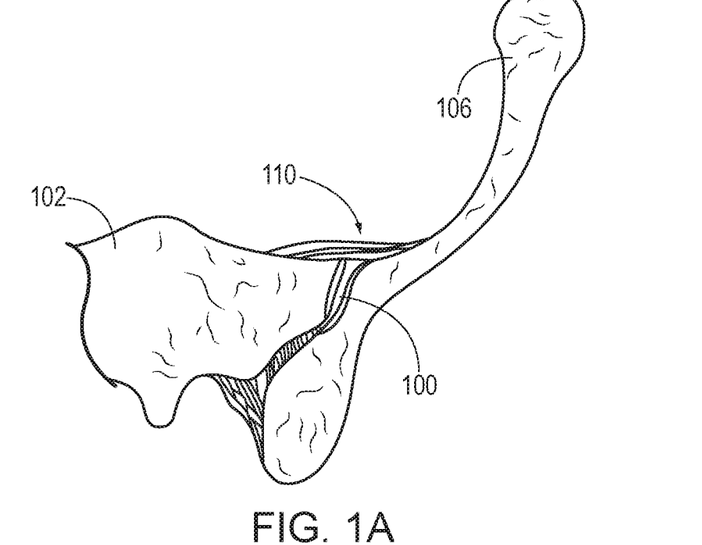
FIG. 1A is a cross-section of the pelvis illustrating the SI joint from an anterior approach.
Figure 1B:
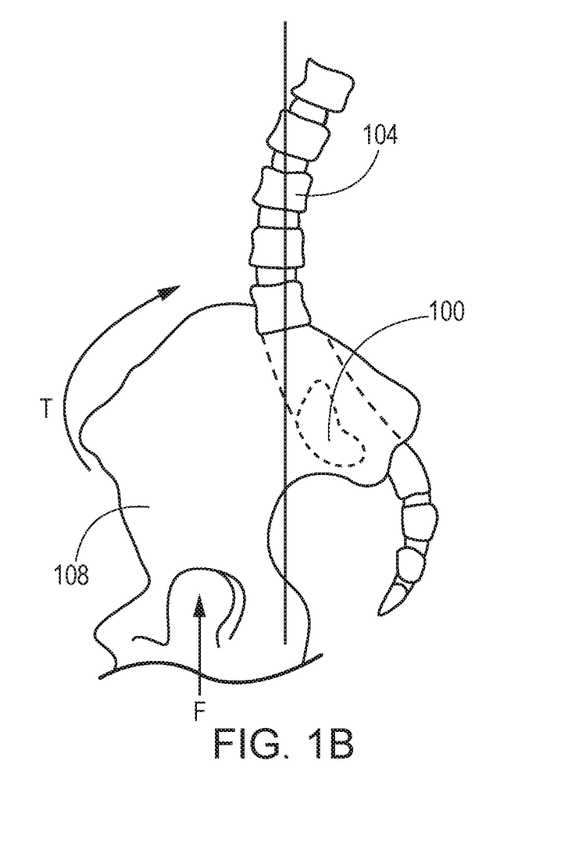
FIG. 1B illustrates the SI joint from a posterior approach.

FIGS. 1A-1B illustrate an SI joint 100, and FIG. 1A is a cross-sectional view of the SI joint 100 from an anterior approach. As shown, the SI joint 100 is located between the sacrum 102 at the base of the spine 104 (see FIG. 1B) and the ilium 106, which is the upper bone of the pelvis 108 (see FIG. 1B), and various ligaments 110 (i.e., sacroiliac ligaments) support the SI joint 100. FIG. 1B illustrates the location of the SI joint 100 from a lateral approach, relative to the spine 104 and the pelvis 108. As shown in FIG. 1B, impact force F from walking and other movements applies a torque T on the SI joint 100, which is depicted with phantom lines between the spine 104 and the pelvis 108. This torque T acting on the SI joint 100 may result in pain if there is dysfunction in the SI joint 100.

Increasingly, fusion procedures (i.e., SI joint fusions) are being performed on the SI joint 100 as a treatment for various conditions and disorders. SI joint fusion immobilizes the SI joint 100 by rigidly connecting the sacrum 102 to the ilium 106, and thereby inhibits application of the torque T on the SI joint 100. Current SI joint fusion techniques incorporate a lateral approach to access the SI joint 100, as illustrated in FIG. 1B, so that a physician may drive a dowel rod or pin through the crest of the ilium 106 (i.e., the iliac crest) into the ala of the sacrum 102 to immobilize the SI joint 100. While the lateral approach is widely utilized by physicians in the field of orthopedics, it is much less common in the field of neurosurgery where physicians often utilize a posterior approach. Thus, physicians performing SI joint fusion tend to be more familiar with posterior approaches than lateral approaches, however, the posterior approach is not presently utilized during SI joint fusion operations. Also, performing SI joint fusion via the lateral approach may not be performed simultaneous with lumbar or spinal operations using posterior approaches. Thus, for example, a physician performing a spinal fusion through a posterior approach to correct a patient's scoliosis will need to perform a separate operation on the patient to fuse the SI joint 100 through the lateral approach.

In addition, many current SI joint fusion techniques do not incorporate bone grafts to strengthen the SI joint 100 when fused, but instead only rely on the strength of the dowel rods and pins to secure the SI joint 100. These dowel rods and pins deteriorate over time and ultimately fail, unless there is a bony fusion, thereby subjecting patients to additional surgery. Also, these dowel rods and pins provide minimal surface contact between the sacrum 102 and the ilium 106 when the SI joint 100 is pulled together, thereby resulting in less bone fusion and less strength in the fused SI joint after healing. Moreover, to the extent that fusion occurs between the sacrum 102 and the ilium 106, these SI joint fusion procedures attempt to fuse cortical bone that does not fuse as well as the cancellous bone underlying the cortical bone.

Accordingly, there remains a need for improved SI joint fusion devices and techniques that overcome the challenges of these prior solutions.

SUMMARY OF THE INVENTION

Presently disclosed is a joint implant. In an embodiment, a joint implant includes a porous body configured to promote bone growth, the body having a porous body with a first face, a second face, and a window extending between the first and second faces. The window is configured to hold a graft material that facilitates bone growth when the implant is maintained in compression with the first face contacting the sacrum and the second face contacting the ilium.

In some embodiments, the implant comprises porous titanium. In some embodiments, the implant includes ridges or rails extending on either or both of the first and second faces, and, in some of these embodiments, the rails extend in the direction of insertion of the implant. In some embodiments, the implant includes a lip extending around the window and, in some of these embodiments, the lip is arranged on the first and/or second face.

Also disclosed herein is a SI joint fusion method. The SI joint fusion method includes the steps of preparing the joint, placing the implant within the SI joint, and then compressing the SI joint. The step of preparing the joint may include reaming or cutting the joint to form a space therein in which the implant may be received.

Also disclosed herein is a sacroiliac joint implant system. The sacroiliac joint implant system may include a pair of fasteners configured to be fixed to opposite sides of the SI joint and a rod extending between and secured by the pair of fasteners. For example, a first fastener may be anchored to the sacrum and a second fastener may be anchored to the ilium and, in some examples, the first fastener is either an S-1 screw or an S-2 alar screw and the second fastener is an iliac screw. The sacroiliac joint implant system also includes an implant having a porous body that is placed within the SI joint and configured to promote bone growth. The porous body of the implant includes a first face configured to contact a sacrum of the sacroiliac joint when the implant is compressed within the sacroiliac joint, a second face configured to contact an ilium of the sacroiliac joint when the implant is compressed within the sacroiliac joint, and a graft window extending between the first and second faces and configured to hold a graft material.

BRIEF DESCRIPTION OF THE FIGURES

The invention can be understood from the following detailed description of exemplary embodiments of the invention taken in conjunction with the accompanying drawings.

DETAILED DESCRIPTION

The present disclosure relates in general to SI joint fusions and, more particularly, to implants and methods for posterior SI joint fusion.

The embodiments described herein provide methods of performing SI joint fusions via posterior approaches (i.e., posterior SI joint fusions). The embodiments described herein also provide reaming guides utilizable in posterior SI joint fusions for defining the tool path and limiting the depth of cut as needed for a particular physiology. In some embodiments, the reaming guides are boxes oriented parallel to the SI joint. Other embodiments described herein provide a fusion plate utilizable in a posterior SI joint fusion and having a window for holding graft material that helps bone grow across the porous fusion plate through the window. In some embodiments, the fusion plate is made from a porous material that helps bone grow into and across the fusion plate, which thereby facilitates bone growth through the plate and bone fusion within the SI Joint.

Figure 2:
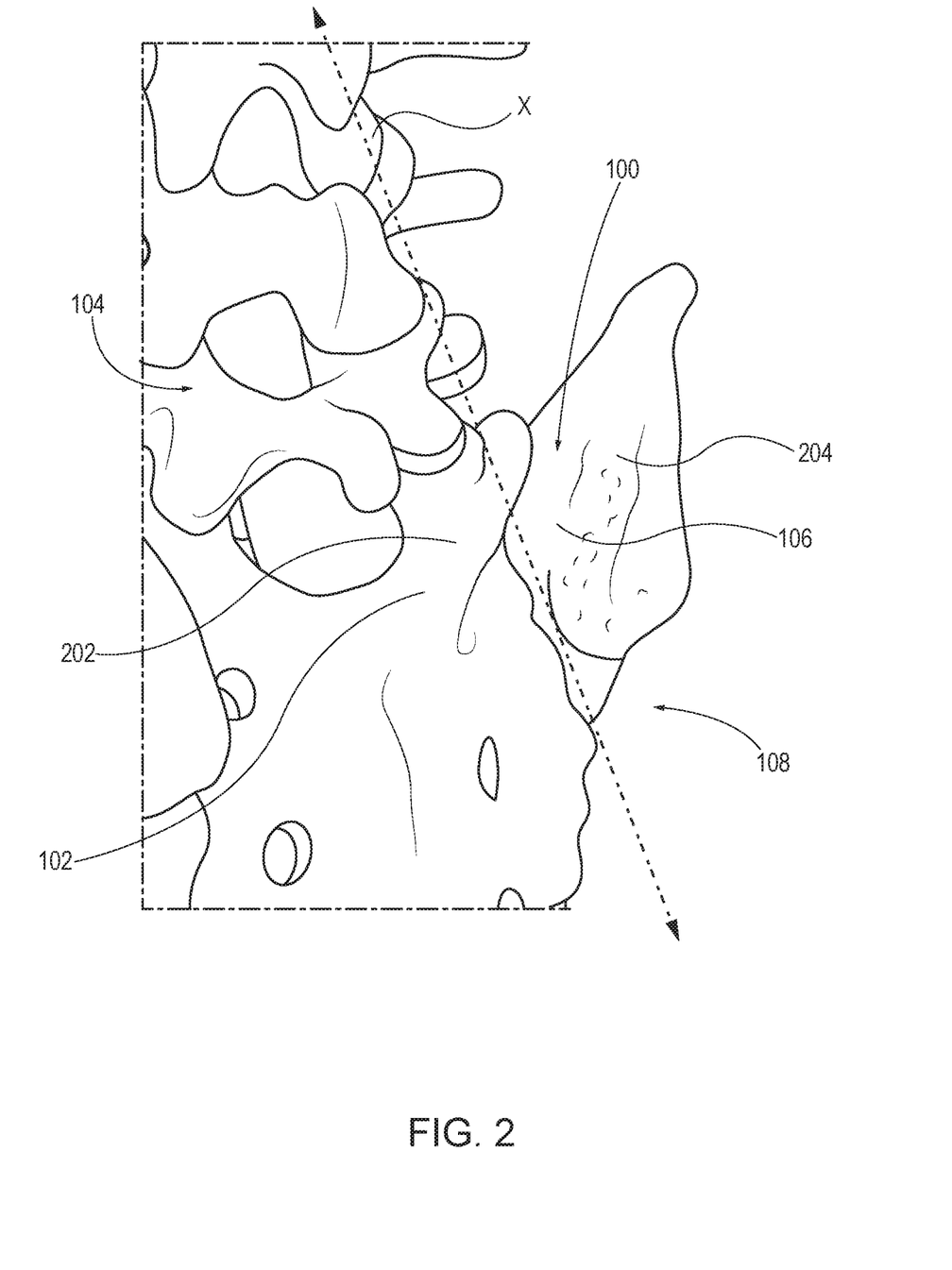
FIG. 2 illustrates the SI joint from a posterior approach.

FIG. 2 is a posterior view of the SI joint 100. Thus, FIG. 2 illustrates the SI joint 100 when accessed posteriorly (i.e., with a posterior approach). Physicians performing spinal fusions in the lumbar region, for example, to correct scoliosis, will utilize the posterior approach and may be provided access to the SI joint 100 as depicted in FIG. 2. In addition, FIG. 2 illustrates the ala 202 of the sacrum 102 and the iliac crest 204 of the ilium 106, and further depicts how the SI joint 100 generally extends along an axis X. The SI joint 100 of FIG. 2 is shown prior to any bone removal as described below. Thus, FIG. 2 shows the cortical bone of the sacrum 102 and the ilium 106.

Figure 5A:
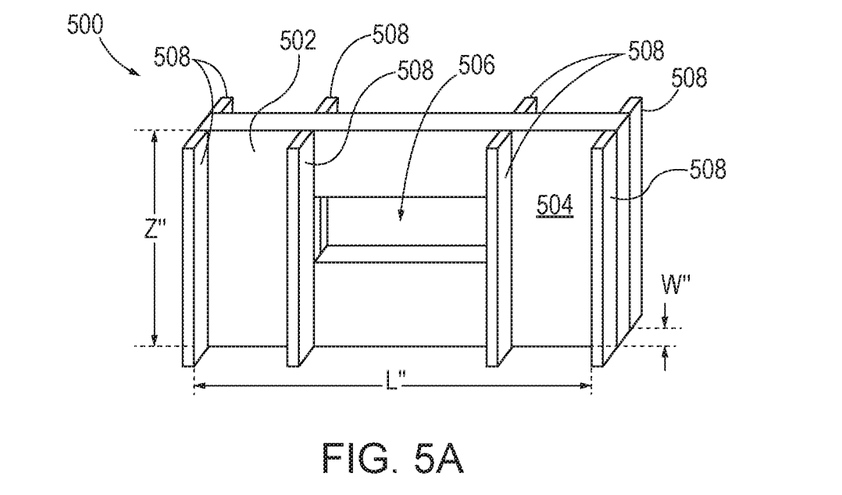
FIG. 5A is an exemplary implant that may be utilized in a SI joint fusion, according to one or more embodiments.

When performing posterior SI joint fusions, an implant (see FIG. 5) may be placed in the SI joint 100. As described below, such implants may facilitate fusion of the SI joint 100 by providing a scaffold for a graft material that will generate bone across the SI joint 100 and, after fully healing, strengthen the fusion across the SI joint 100. Before placing the implant within the SI joint 100, however, the SI joint 100 may be prepared such that there is sufficient space to receive the implant.

Figure 3:
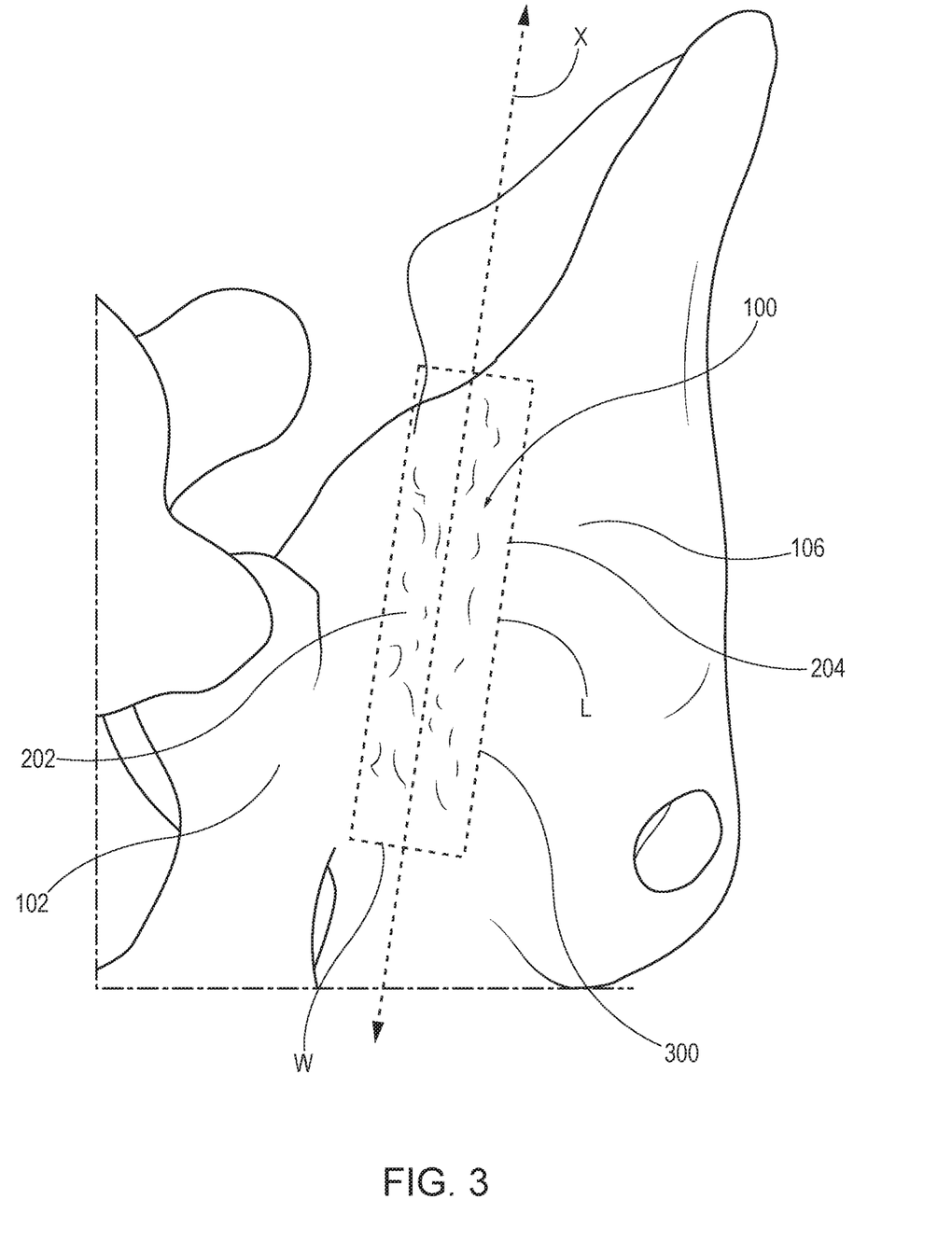
FIG. 3 illustrates the SI joint 100 of FIG. 2 after having been prepared by forming a space therein.

FIG. 3 illustrates the SI joint 100 of FIG. 2 after being prepared, according to one or more embodiments of the present disclosure. As illustrated, a space 300 was formed at the SI joint 100 for receiving the implant. The space 300 has a length dimension L, a width dimension W, and a depth dimension (not illustrated) that is normal to the length and width dimensions W, L. Here, the space 300 is formed generally parallel the SI joint 100, meaning that the length dimension L of the space 300 is parallel to the axis X of the SI joint 100. Also, the dimensions of the space 300 may vary depending on the size of the implant. For example, the width dimension W of the space 300 may be sized to correspond with a width of the implant such that the implant may be inserted into the space 300.

A variety of methods and tools may be utilized to form the space 300 in the SI joint 100. In the illustrated examples, the SI joint 100 was prepared via a reaming procedure. In the reaming procedure, a rotational cutting tool (e.g., a reamer) is utilized to cut portions of the sacrum 102 and the ilium 106 on either side of the SI joint 100, and thereby define the space 300 into which the implant may be inserted. During the reaming procedure, the cortical bone layers of the sacrum 102 and the ilium 106 are removed to expose the underlying cancellous bone, which more readily fuses across the SI joint 100 as compared to the cortical bone. Thus, the width dimension W of the space 300 is mostly defined by the distance between exposed cancellous bone of the sacrum 102 and the ilium 106.

A guiding tool may be utilized in the reaming procedure to control the dimensions of the space 300. The guiding tool may provide an envelope or template that guides and limits movement of the rotary cutting tool as it cuts the space 300. For example, the guiding tool may be utilized to form the space 300 according to specific length and width dimensions L, W, and may also limit the rotary cutting tool's depth of cut to control the depth dimension of the space 300. The guiding tool may be made from various materials, including without limitation, stainless steel alloys, commercially pure titanium, titanium alloys, etc.

Figure 4A:
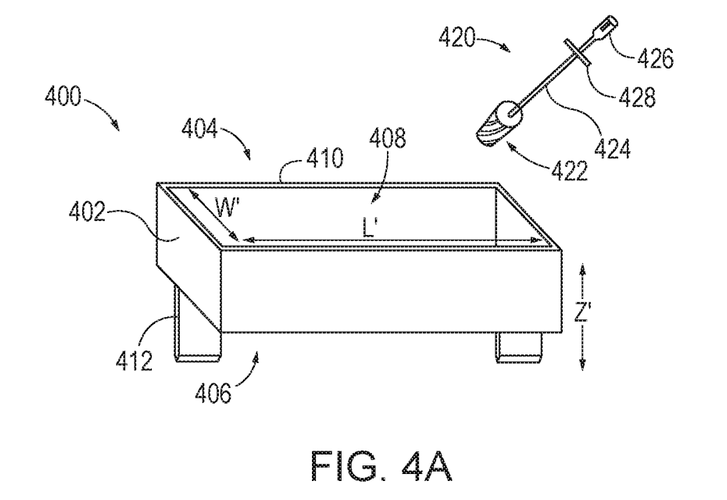
FIG. 4A illustrates a guiding tool that may be utilized in a reaming procedure to form the space in the SI joint as illustrated in FIG. 3, according to one or more embodiments of the present disclosure.

FIG. 4A illustrates an exemplary guiding tool 400, according to one or more embodiments of the present disclosure. Here, the guiding tool 400 includes a body 402 having a proximal side 404 and a distal side 406. Here, the body 402 is configured as a box shaped member with an opening 408 extending through the body 402 from the proximal side 404 to the distal side 406. The body 402 includes a rim 410 extending around the opening 408 at the proximal side 404. The guiding tool 400 also includes at least one mounting feature for securing the guiding tool 400 to bone relative to the SI joint 100. Here, the guiding tool 400 includes a pair of mounting posts 412 that may be driven into the bone of the pelvis 108 with a mallet to anchor the guiding tool 400 relative to the SI joint 100; however, the mounting feature may be differently configured. For example, the mounting features may include one or more phalanges, screws, etc. or combinations of the same. In the illustrated example, the mounting posts 412 include flat surfaces that are oriented with the SI joint 100, generally parallel to the axis X of the SI joint 100, such that they may more easily slide into the SI joint 100. Here, the mounting posts 412 are positioned centered on a sidewall of the body 402, but they may be positioned differently along the sidewall (or another sidewall) of the body 402. Thus, the guide 400 may be configured to slide into the SI joint 100, with the mounting posts 412 sliding therein between the cortical surfaces of the SI joint 100 to keep the guiding tool 400 oriented so that there is an even cut from both the iliac crest surface and the sacral surface. However, the mounting posts 412 may have various other configurations relative to the axis X of the SI joint 100, which may help secure the guiding tool 400 within the SI joint 100.

During the reaming procedure, the distal side 406 of the guiding tool 400 is secured over the SI joint 100 and a rotary cutting tool 420 may be inserted through the opening 408 such that the rotary cutting tool 420 may access the SI joint 100 positioned beneath the guiding tool 400. As illustrated, the rotary cutting tool 420 includes a cutting edge 422 positioned at a distal end thereof, a shaft portion 424 extending proximally from the cutting edge 422, and a shank 426 extending proximally from the shaft portion 424 for mounting the rotary cutting tool 420 within a driver or other equipment. The rotary cutting tool 420 also includes a stopper 428 positioned on the shaft portion 424 and is configured to limit the depth that the cutting edge 422 may extend distally beneath the guide tool 400. In the illustrated example, the stopper 428 is a flange member that, during the reaming procedure, abuts and contacts the rim 410 of the body 402, thereby inhibiting further distal translation of the cutting edge 422 and limiting the depth at which it extends into the SI joint 100.

The size of the space 300 formed in the SI joint 100 during the reaming procedure is controlled by the guiding tool 400. More particularly, the rotary cutting tool 420 cuts the space 300 with length and width dimensions L, W corresponding to a width W' and length L' of the opening 408 in the box shaped body 402 of the guiding member 400. In addition, the depth dimension of the space 300 formed in SI joint 100 is controlled by a vertical dimension Z' of the guiding tool 400, which may be influenced by various parameters of the rotary cutting tool 420, such as the distance at which the cutting edge 422 extends distally from the stopper 428, etc.

Figure 4B:
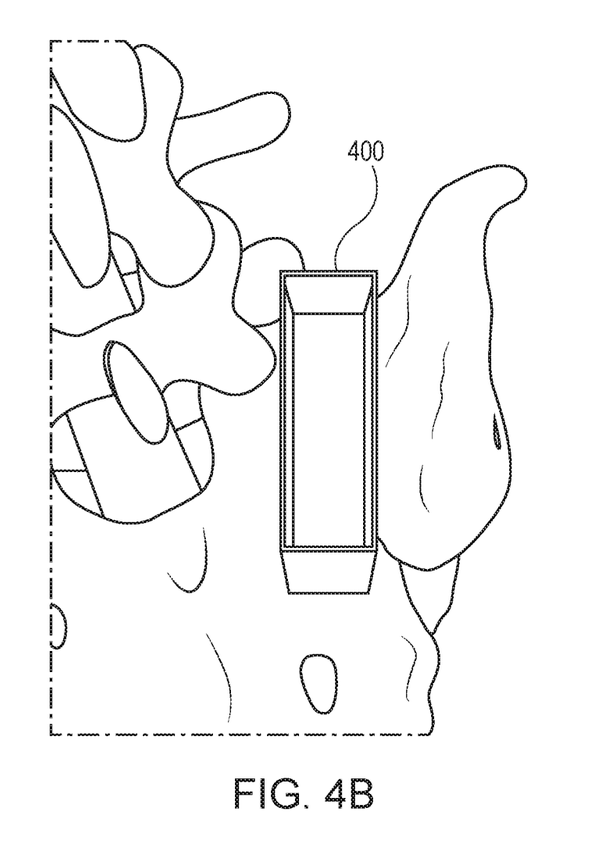
FIG. 4B illustrates a posterior view of the guiding tool of FIG. 4A positioned parallel to the SI joint prior to the reaming procedure to form the space in the SI joint as illustrated in FIG. 3.
Figure 4C:
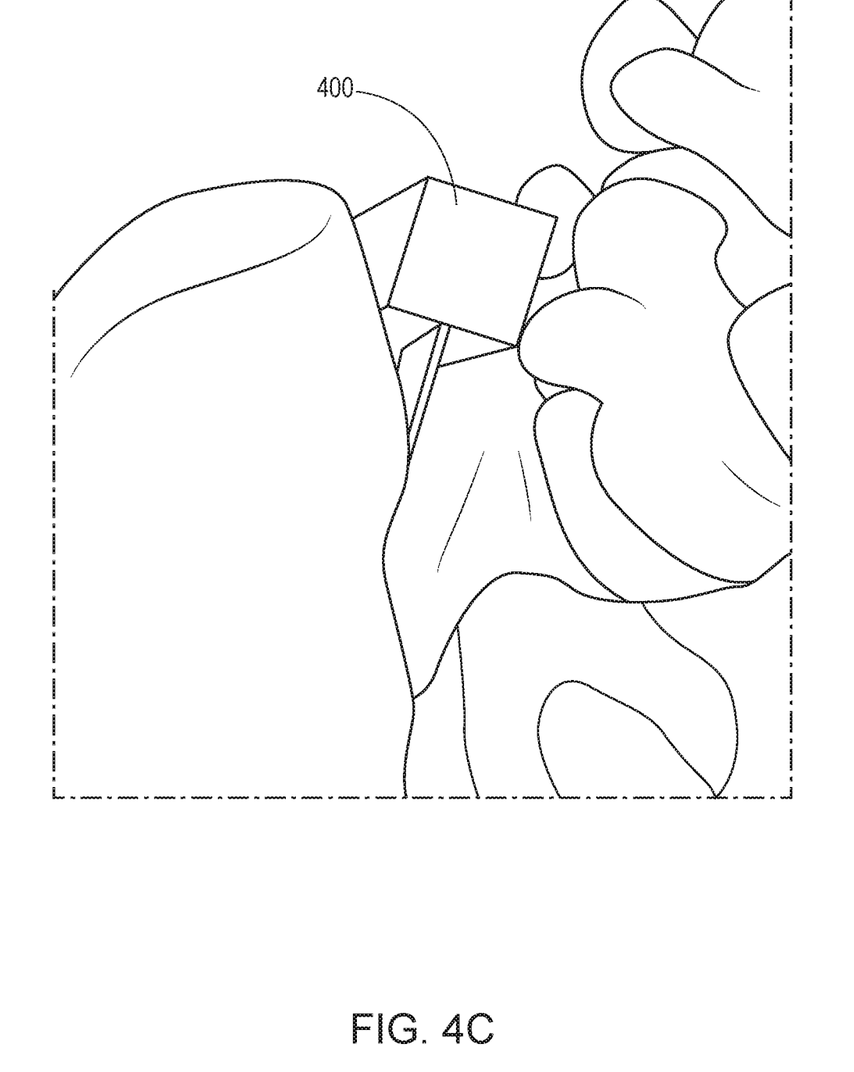
FIG. 4C is a superior anterior view of FIG. 4B.

As illustrated in FIG. 4B, the guiding tool 400 is positioned parallel to the SI joint 100. Thus, the length L' of the opening 408 is aligned with the axis X of the SI joint 100 such that the guiding tool 400 and the SI joint 100 are parallel. Various techniques and/or equipment may be utilized to position the guiding tool 400 before anchoring it to the SI joint 100. In one example, a stereotactic computer aided guidance system (not illustrated) is utilized. Here, the guiding tool 400 may include one or more sensors that communicate with the stereotactic computer aided guidance system to allow placement of the guiding tool 400 in a desired position and orientation relative to the SI joint 100.

Figure 5B:
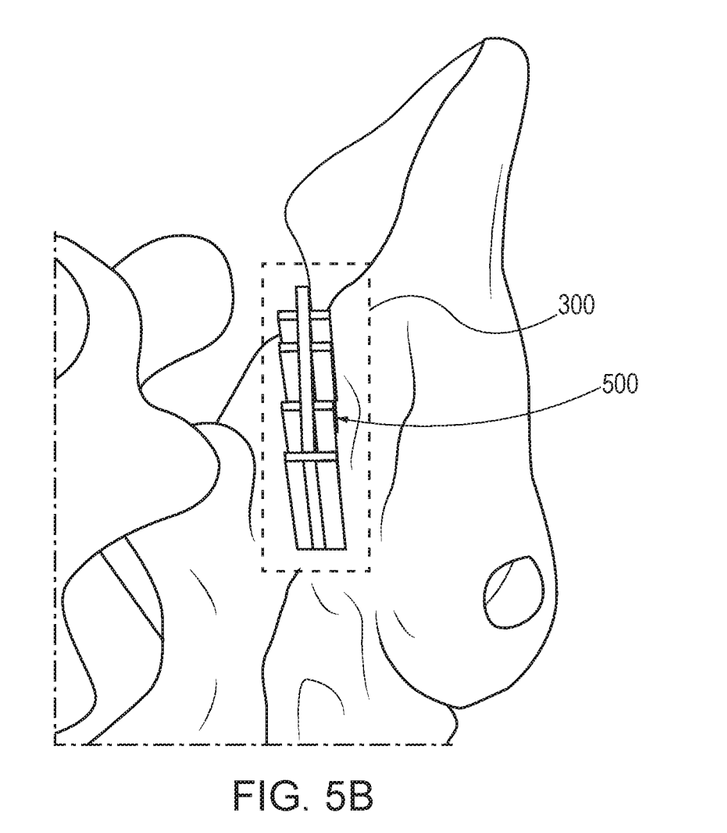
FIG. 5B illustrates a posterior view of the implant of FIG. 5A placed within the space of the SI joint as illustrated in FIG. 3.
Figure 5C:
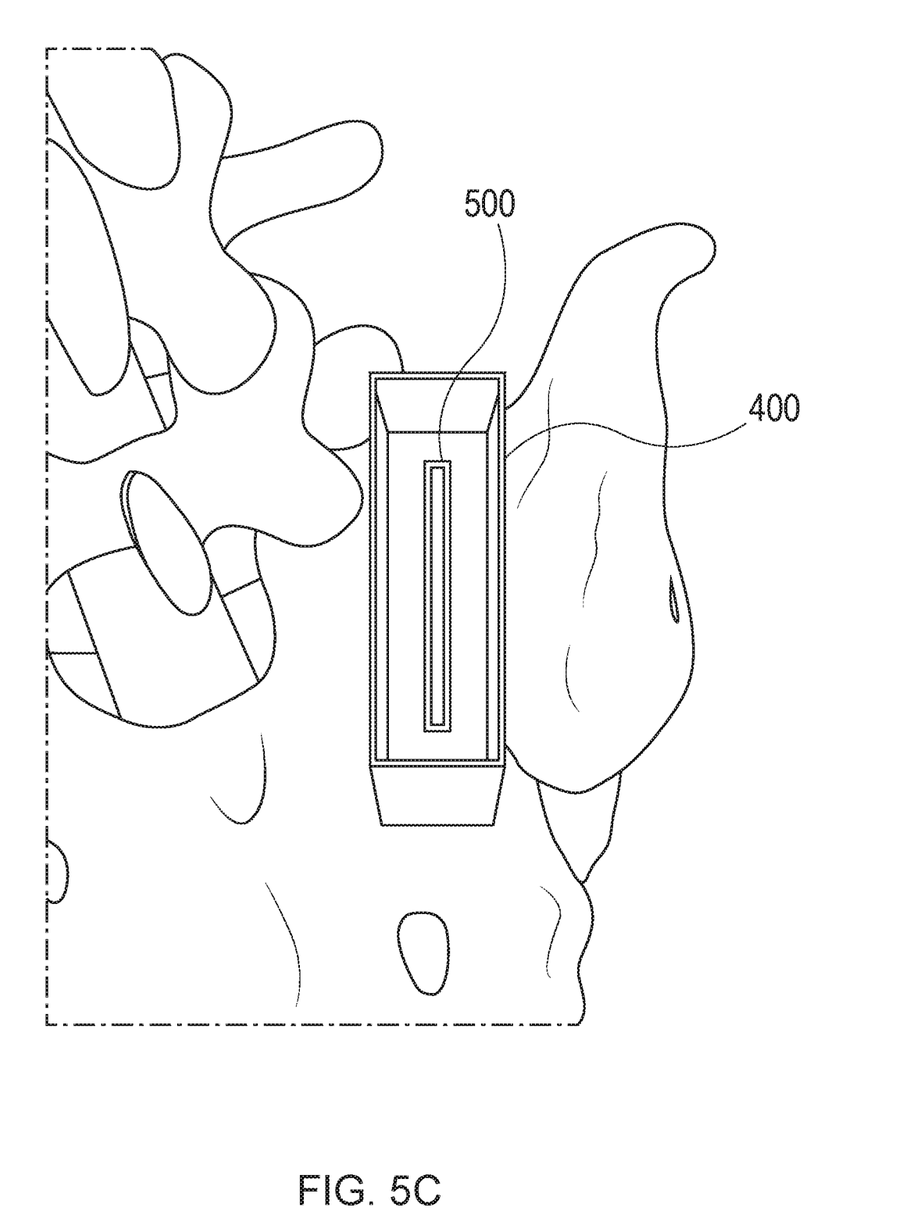
FIG. 5C illustrates a posterior view of the implant of FIG. 5A inserted through the guiding tool of FIG. 4A and placed within the space of the SI joint as illustrated in FIG. 3.

After the SI joint 100 has been prepared by cutting the space 300 therein, the implant may be placed therein to facilitate fusing the SI joint 100. FIG. 5A illustrates an exemplary implant 500 that may be fused in the SI joint 100, according to one or more embodiments of the present disclosure. Here, the implant 500 is a plate 502 with first face 504, a second face (obscured from view) opposite from the first face 504, and a graft window 506 extending therethrough between the first face 504 and the second face. The plate 502 may be made from a porous material. FIG. 5B illustrates the implant 500 of FIG. 5A having been inserted into the space of FIG. 3 via a posterior approach. FIG. 5C illustrates the implant 500 of FIG. 5A having been inserted through the guiding tool 400 of FIG. 4A and into the space of FIG. 3 via a posterior approach.

The implant 500 may have various geometries and shapes. For example, the first face 504 and/or the second face may be concave or convex. In one example, the first face 504 and the second face are both flat, but in other examples, they are biconvex and, in some of these latter examples, the implant 500 is pointed in the direction of insertion and opens up posteriorly like a cup. In some examples, the first face 504 and/or the second face include both concave and convex portions that correspond with the particular geometry of the portion of the SI joint 100 that they are configured to abut when compressed therein. For example, a particular patient's SI joint 100 may be scanned and modeled in a CAD software, and then the implant 500 may be designed to best correspond and fit that particular patient's SI joint 100 geometry and then printed and surgically installed in the patient's SI joint 100. Thus, the implant 500 may have a customized geometry and size corresponding with the actual geometry of a patient's SI joint 100 and the first face 504 and/or the second face may be contoured to correspond with contours of the particular patient's SI joint 100. However, the implant 500 also be provided in standard sizes and geometries.

The implant 500 may also have various shapes. Here, the plate 502 is square shaped with approximately ninety degree (90°) corners, but the corners may have various other geometries. For example, one or more of the corners may be rounded, chamfered, etc. Also, the plate 502 may have various other non-square or non-rectangular shapes, such as circular, oval, etc., however, the implant 500 may be custom 3D printed such that the plate 502 may conform or fit anatomic variants or joints that had previous surgeries. Thus, the implant 500 and the plate 502 thereof may be customized to the particular patient and may thus have any number of shapes or geometries. In some examples, the plate 502 is shaped to fit a particular patient's SI joint 100. Here, the implant 500 includes various dimensions, including a width dimension W", a length dimension L", and a vertical dimension Z". The implant 500 may be provided with various sizes depending on the particular size of the space 300 into which the implant 500 is to be placed. However, the thickness of the plate 502 should be sufficient to cross the SI joint 100 and enter the cancellous bone exposed after the reaming procedure cut away the layer of cortical bone. For example, the thickness of the plate 502 may vary to allow maximum bony surface contact between the implant 500 and the SI joint 100. Also, where the guide tool 400 is utilized to form the space 300 in the SI joint 100, the implant 500 may be inserted into the space 300 in the SI joint 100 through the opening 408 in the box shaped body 402 (FIG. 5C). Thus, in such embodiments, the implant 500 may be sized to fit within the guiding tool 400 and may even be provided together as a kit for SI joint fusions. Alternatively, the implant 500 may be inserted directly into the SI joint 100 (FIG. 5B) and, in such examples, the guiding tool 400 would be removed from the SI joint 100 or not utilized at all to form the space 300 therein.

The plate 502 may be formed of a porous material selected to promote bone growth. In one embodiment, the plate 502 is formed of porous titanium with a modulus similar to natural bone. In other embodiments, selected portions of the plate 502 are formed of porous material while other portions are formed of non-porous materials. In some embodiments, the plate 502 is formed by an additive manufacturing process, such as 3D printing. In some embodiments, the porous material forms a lattice having pores of approximately 0.75 millimeter in diameter. The graft window 506 is configured to receive a graft material. For examples, the graft window 506 may be filled with either autologous or allograft. The graft window 506 allows for the fusion to grow through the implant 500 and the porous material from which the body 502 is manufactured allows fusion to grow into and through the plate 502.

The implant 500 may include various features for strengthening the plate and/or helping secure the plate within the SI joint 100. For example, the implant 500 may have various features and/or designs that prevent micromotion and allow maximum contact with the bone of the SI joint 100. In the illustrated examples, the implant 500 includes a plurality of rails or ridges 508 oriented in the direction at which the implant 500 is to be inserted into the space 300 of the SI joint 100. The rails or ridges 508 may be made of the same porous material as the remainder of the implant 500 to allow in growth into and through the ridges 508. Thus, the ridges 508 extend from a top edge 510 to a bottom edge of the plate 502. The ridges 508 may help secure the implant 500 within the SI joint 100 by providing a friction fit and inhibit it from sliding such that the ridges 508 remove at least one degree of freedom of movement of the implant 500 when installed in a patient's SI joint 100. In addition, the ridges 508 may help the implant 500 slide down, with the top edge 510 or the bottom edge 510 leading, into the SI joint 100. In some examples, the ridges 508 may include serrations or other features that allow the implant 500 to slide into the SI joint 100 but inhibit the implant 500 from backing out after being inserted into the SI joint 100. For example, the ridges 508 may include triangular serrations with a flat side posterior and pointed anterior to ease insertion into the SI joint 100. Here, four (4) ridges 508 extend from the first face 504 of the plate 502 and four (4) ridges 508 extend from the second face of the plate 502. As illustrated, the ridges 508 provide the implant 500 with an "I-beam" configuration, and are positioned proximate to the lateral edges of the plate 502 and proximate to the lateral edges of the graft window 506. However, more or less of the ridges 508 may be utilized. For example, just the lateral edge ridges 508 or the ridges 508 sandwiching the graft window 506 may be included, or the implant may include ridges 508 on only one side (e.g., the first side 504) of the plate 502. Also, the ridges 508 may have one or more different geometries than the generally straight rail members illustrated in the figures. Moreover, the plate 502 may have various textures, such as asperities or other features that help create friction. For example, the first face 504 and/or second face may include asperities.

The implant 500 may include various features for helping secure the graft material within the graft window 506. Where utilized, the ridges 508 disposed proximate the graft window 506 may also help maintain the graft material within the graft window 506. In addition, the plate 502 may include a lip portion (not illustrated) extending around at least a portion of the graft window 506 to help maintain the graft material within the graft window 506, and such lip portion may be included with or without the one or more ridges and/or other features. In some examples, one or more sutures (not illustrated) may be wrapped around the plate 502 to help retain the graft material within the graft window 506. For example, a first suture may be wrapped around the plate 502 in the length dimension L" and a second suture may be wrapped around the plate 502 in the vertical dimension Z" such that the first and second sutures cross each other at the graft window 506. More or less sutures may be utilized, however, and they may be wrapped differently around the plate 502 without departing from the present disclosure. Also, in some examples, one or more structures (not illustrated) connected to the plate 502 may be arranged across the graft window 506. Where utilized, such structures may have various orientations (e.g., arranged along the length, vertical, and/or width dimensions L", Z", W"), and such structures may support various sub-structures suspended within the graft window 506, any of which may be provided to facilitate bone growth and fusion.

When the implant 500 is installed in a patient, the plate 502 contacts the sacrum 102 and the ilium 106 under pressure. By applying pressure at the points of contact, the implant 500 achieves compression that promotes bone growth in a manner not previously possible with posterolateral vertebrae fusion devices. In this manner, the presently disclosed implant 500 may achieve an improved rate of fusion. Thus, after the SI joint 100 has been prepared and the implant 500 has been placed within the space 300 cut into the SI joint 100, the SI joint 100 will be compressed. Compression will facilitate SI joint fusion because, pursuant to Wolf's law, compression across a fusion device yields the greatest fusion.

Various fasteners may be utilized to compress the implant 500 within the space 300 of the SI joint 100. For example, pedicle screws may be installed within the surgical site of the patient and connected with rods that are compressed with compression devices to squeeze the SI joint 100 and sandwich the implant 500 therein. The various pedicle screws may be placed at various times during the SI joint fusion. For example, they may be placed at the beginning of the procedure, at various times before preparing the joint, at various times after preparing the joint but before inserting the implant 500 therein, or after inserting the implant 500 within the space 300 previously formed in the SI joint 100, etc.

Figure 6A:
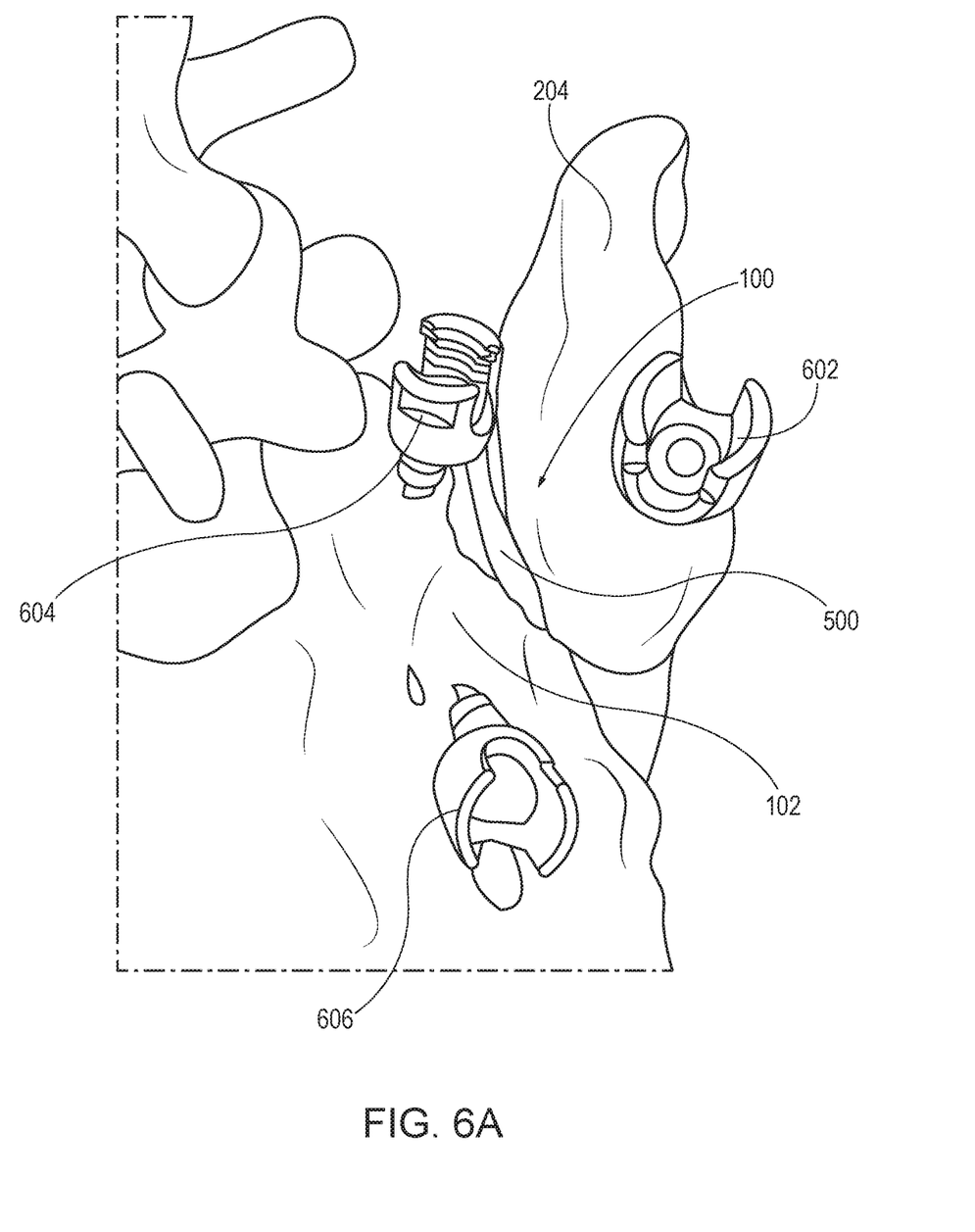
FIG. 6A illustrates exemplary placement of fasteners about the SI joint.

FIG. 6A illustrates exemplary screw placement about the SI joint 100, according to one or more embodiments. In particular, FIG. 6A illustrates placement of an iliac screw 602 in the iliac crest 204, as well as an S-1 screw 604 and an S-2 alar screw 606 placed in the sacrum 102. As described below, a rod may be placed to bridge the SI joint 100 and interconnect either the iliac screw 602 and the S-1 screw 604 or the iliac screw 602 and the S-2 alar screw 606. Thus, both the S-1 screw 604 and the S-2 alar screw 606 need not be placed during the same SI joint fusion operation to apply compression to the implant 500 placed in the space 300 of the SI joint 100, and either the S-1 screw 604 or the S-2 alar screw 606 may be utilized depending on which may provide best compression in a particular fusion operation. For example, either the S-1 screw 604 or the S-2 alar screw 606 may be utilized depending on which will orient the rod more perpendicular to the structure of a patient's SI joint 100 when connected to the iliac screw 602. However, in some long segment operations, such as a scoliosis operation, a first rod may be placed between the S-1 screw 604 and the S-2 alar screw 606 and then a lateral rod may attach to a mid-point of the first rod and connect to the iliac screw 602 and thereby bridge the SI joint 100 as described below with reference to FIG. 6C.

Figure 6B:
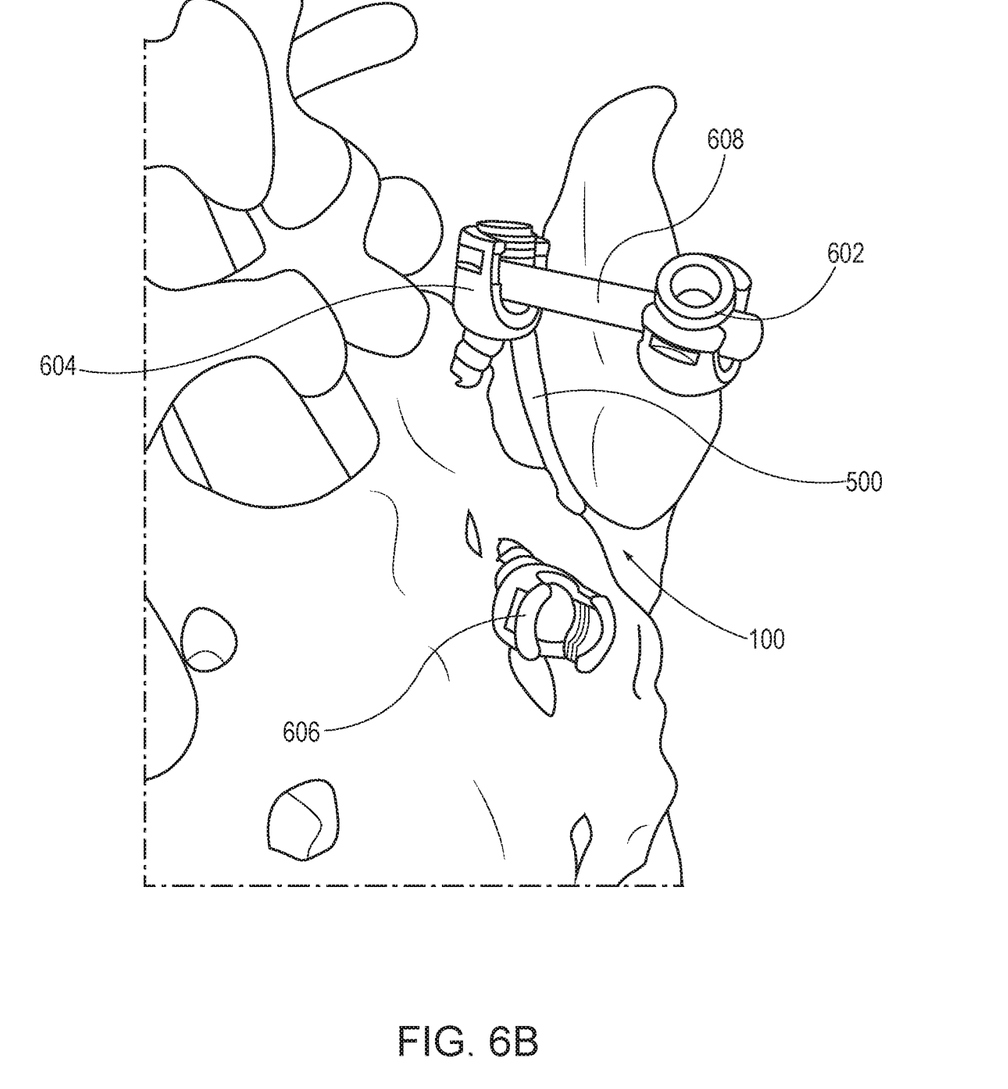
FIG. 6B illustrates exemplary placement of a rod installed within the fasteners of FIG. 6A to apply compression to the SI joint.

FIG. 6B illustrates an exemplary lateral rod 608 placement, according to one or more embodiments. Here, the lateral rod 608 has been placed in the screw heads of the iliac screw 602 and the S-1 screw 604. However, as mentioned above, the lateral rod 608 may instead be installed in the head of the S-2 alar screw 606 and bridge the SI joint 100 to interconnect to the head of the iliac screw 602, or the lateral rod 608 may be a lateral connecting rod spanning between the head of the iliac screw 602 and another rod (i.e., a long segment rod) installed between S-1 screw 604 and the S-2 alar screw 606. Once the one or more rods have been placed in the screw heads, a compression device (not illustrated) may be utilized to compress the SI joint 100 via the pedicle screws and rods and thereby squeeze the implant 500 within the space 300 of the SI joint 100.

Figure 6C:
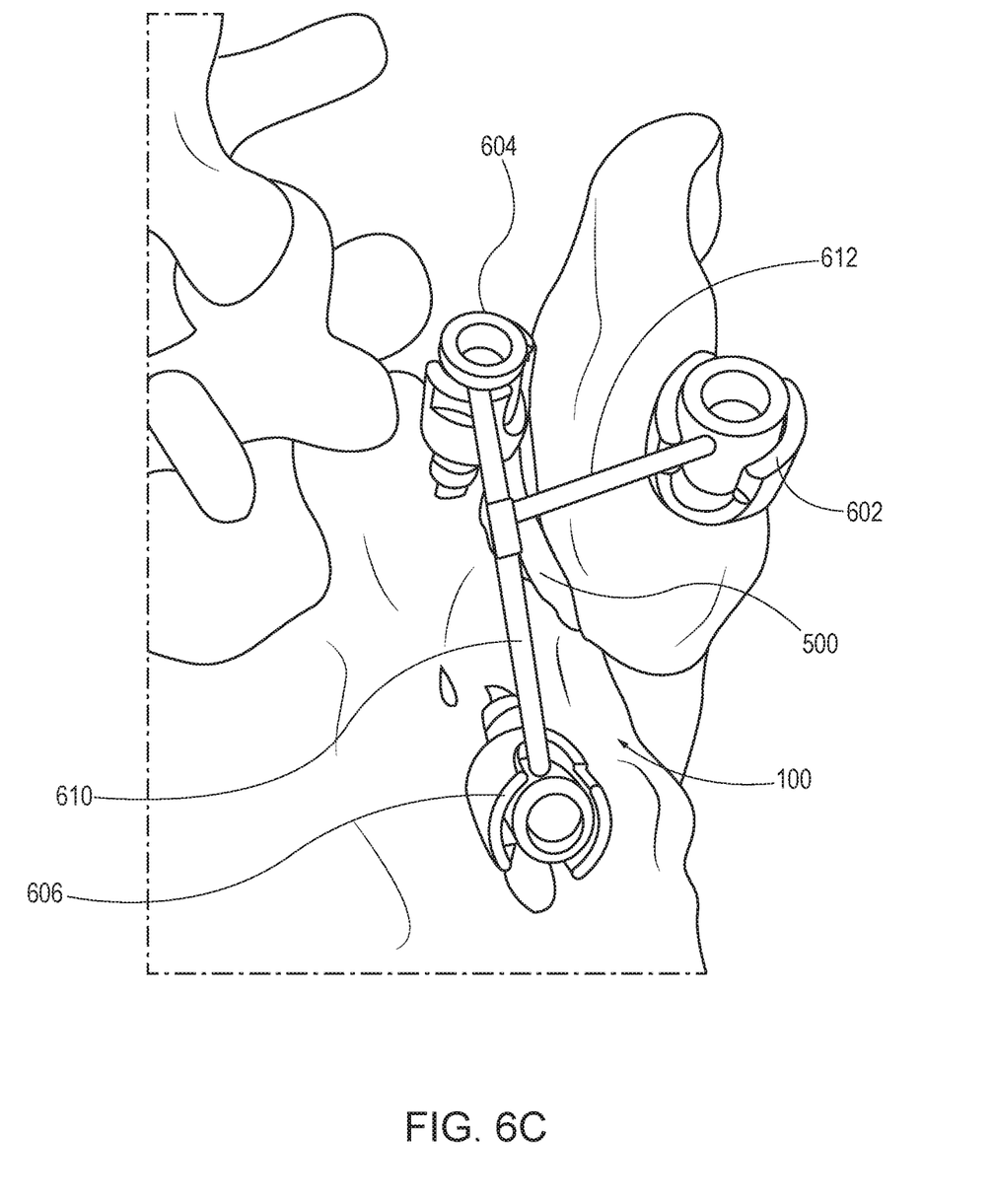
FIG. 6C illustrates an exemplary placement or a rod and lateral rod within the fasteners of FIG. 6A to apply compression to the SI joint during a long segment operation, according to one or more embodiments.

FIG. 6C illustrates an exemplary placement of a long segment rod 610 and a lateral rod 612 in a long segment operation, according to one or more embodiments. As illustrated, the long segment rod 610 is placed between the S-1 screw 604 and the S-2 alar screw 606, and the lateral rod 612 is secured within the head of the iliac screw 602 and spans the SI joint 100 by connecting to a portion of the long segment rod 610 between the S-1 screw 604 and the S-2 alar screw 606. While not illustrated, in these long segment operations, additional rods similar to the long segment rod 610 may extend superiorly and/or inferiorly, from either or both the S-1 screw 604 and the S-2 alar screw 606, to other pedicle screws secured along other portions of the spine. Once the lateral rod 612 has been placed in the screw head of the iliac screw 602 and connected to the long segment rod 610, a compression device (not illustrated) may be utilized to compress the SI joint 100 and thereby squeeze the implant 500 within the space 300 prepared therein.

Also disclosed herein is a method for performing an SI joint fusion. The method of fusing the SI joint, sometimes referred to as the SI joint fusion method, includes a first step of preparing the joint, a second step of placing an implant within the SI joint, and a third step of compressing the SI joint. The SI joint fusion method, however, may include one or more additional steps performed before or after the SI joint fusion method, or performed in between any of the foregoing steps. For example, the SI joint fusion method may include an additional step of placing pedicle screws about the SI joint, and such additional step of placing the pedicle screws may be performed at any time before the step of compressing the SI joint or it may be included as part of the step of compressing the SI joint.

The first step of preparing the joint is performed to ensure that there is adequate space within the SI joint to receive the implant. As previously described, a reaming procedure may be utilized to cut the space 300 within the SI joint 100. Also as previously described, the guiding tool 400 may be utilized to control the dimensions of the space 300 cut into the SI joint 100 during the reaming procedure. Thus, the first step of preparing the joint may include placing and installing the guiding tool 400 relative to the SI joint 100. In addition, the pedicle screws may be placed about the SI joint 100 during this step, or at other times during the SI joint fusion method.

The second step of placing an implant within the SI joint is performed to place an implant within the SI joint that permits a bone graft to grow across the SI joint 100, thereby improving and strengthening the fusion after healing. Various types of implants may be utilized, such as the implant 500 described above. Also, in examples where the guiding tool 400 is utilized, the implant 500 may be inserted into the SI joint 100 through the opening 408 in the guiding tool 400. Thus, the second step of placing an implant within the SI joint may include inserting the implant 500 through the guiding tool 400 and into the space 300 prepared in the SI joint 100 and/or positioning the implant 500 within the space 300 prepared in the SI joint 100 via the guiding tool 400, etc. In addition, the pedicle screws may be placed about the SI joint 100 during this step, or at other times during the SI joint fusion method.

The third step of compressing the SI joint is performed to compress the implant across the SI joint 100 because, according to Wolf's law, such compression will provide the greatest fusion. This step may include placing the pedicle screws about the SI joint 100; however, such pedicle screws may be placed during any of the preceding steps, or before the SI joint fusion method altogether, for example, during a long segment operation to correct scoliosis, which may be conducted immediately prior to the SI joint fusion method. This step may include bridging the SI joint 100 by placing a lateral rod (e.g., the lateral rod 608 or the lateral rod 612) across the SI joint 100, as previously described, and then using a compression device to compress the SI joint 100 and the implant 500 previously inserted therein. As described above, the lateral rod 608 may be placed within the heads of the iliac screw 602 and the S-1 screw 604 (FIG. 6B) or within the heads of the the iliac screw 602 and the S-2 alar screw 606. Alternatively, the lateral rod 612 may be placed in the head of the iliac screw 602 and connect to the long segment rod 610 spanning between the S-1 screw 604 and the S-2 alar screw 606 (FIG. 6C). Thus, this step may also include placing the long segment rod 610 before bridging the SI joint 100 with the lateral rod 612, as previously described; however, placing the long segment rod 610 may be performed during any of the preceding steps or before the SI joint fusion method altogether.

Also disclosed herein is a sacroiliac joint implant system. The sacroiliac joint implant system may include a pair of fasteners configured to be fixed to opposite sides of the SI joint 100 and a lateral rod securable within the pair of fasteners. For example, a first fastener may be anchored to the sacrum and a second fastener may be anchored to the ilium and, in some examples, the first fastener is either an S-1 screw or an S-2 alar screw and the second fastener is an iliac screw. In some examples, the sacroiliac joint implant system includes three or more fasteners. For example, the sacroiliac joint implant system may include an S-1 screw, an S-2 alar screw, and an iliac screw; and, in such embodiments, the sacroiliac joint implant system may also include one or more long segment rods and/or a lateral rod configured to attach to a long segment rod, as described above.

The sacroiliac joint implant system may also include one or more implants, any of which may be configured as described with reference to the implant 500. Thus, the implant of the sacroiliac joint implant system may have a porous body that is placed within the SI joint and configured to promote bone growth. The porous body of the implant includes a first face configured to contact a sacrum of the sacroiliac joint when the implant is compressed within the sacroiliac joint, a second face configured to contact an ilium of the sacroiliac joint when the implant is compressed within the sacroiliac joint, and a graft window extending between the first and second faces and configured to hold a graft material.

The sacroiliac joint implant system, or portions thereof may be provided as a "kit." For example, a kit of implants may also be provided that includes a selection of implants of different sizes. In some examples, the kit includes digital instructions or schematics for a 3D printer, or the like, which a user may utilize to print (or create) the implant. The kit may also include one or more guiding tools having corresponding sizes to receive the implant(s), and may also include a rotary cutting tool configured to operate within the envelope defined by the guiding tool. In some examples, the kit includes digital instructions or schematics for a 3D printer, or the like, which a user may utilize to print (or create) the guiding tool. In addition, the kit may include various pedicle screws and various types of connecting rods for applying compression to the SI joint. A surgeon may select the implant, guiding tool and rotary cutting tool, screws, connecting rods best suited to the particular size and geometry of the patient's SI joint. In this manner, the presently disclosed implant may be used in treatment of a wide variety of applications.

The presently disclosed implant may provide numerous advantages for SI joint fusion. An implant formed of porous titanium manufactured with an additive manufacturing process may allow bone growth into it and participate in the fusion. The implant has a pore structure that allows bone growth. Local bone may be trapped within the implant creating a compressed area that would further augment the fusion.

The components of the implant 500 and/or the guiding tool 400 may be fabricated from biologically acceptable materials suitable for medical applications, including metals, synthetic polymers, ceramics and bone material and/or their composites. For example, the components of the implant 500 and/or the guiding tool 400, individually or collectively, can be fabricated from materials such as stainless steel alloys, commercially pure titanium, titanium alloys, Grade 5 titanium, super elastic titanium alloys, cobalt-chrome alloys, stainless steel alloys, super elastic metallic alloys (e.g., Nitinol, super elasto-plastic metals, such as GUM METAL®. manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO.sub.4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-(3), osteoblast cells, growth and differentiation factor (GDF), insulin-like growth factor 1, platelet-derived growth factor, fibroblast growth factor, or any combination thereof.

Various components of the implant 500 and/or the guiding tool 400 may have material composites, including the above materials, to achieve various desired characteristics such as strength, rigidity, elasticity, compliance, biomechanical performance, durability and radiolucency or imaging preference. The components of the implant 500 and/or the guiding tool 400, individually or collectively, may also be fabricated from a heterogeneous material such as a combination of two or more of the above-described materials. The components of the implant 500 and/or the guiding tool 400 may be monolithically formed, integrally connected or include fastening elements and/or instruments, as described herein. In one embodiment, the implant 500, as described herein, may be formed substantially of a biocompatible metal, such as titanium and selectively coated with a bone-growth promoting material, such as HA. In one embodiment, the implant 500, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the implant and/or improve bony on growth to the spinal implant by application of a porous or semi-porous coating of titanium.

Aspects of the presently disclosed implant and methods of SI joint fusion are further illustrated in the images and figures attached as an appendix, which is incorporated herein.

While principles and modes of operation have been explained and illustrated with regard to particular embodiments, it must be understood, however, that this may be practiced otherwise than as specifically explained and illustrated without departing from its spirit or scope.

What is claimed is:

1. A sacroiliac joint implant system for a sacroiliac joint, the sacroiliac joint implant system comprising:
   at least a pair of pedicle screws mounted on opposite sides of the sacroiliac joint;
   a rod extending across the sacroiliac joint, wherein the rod is secured by the pair of pedicle screws; and
   a sacroiliac joint implant having a porous body configured to promote bone growth and fuse the sacrum and ilium of the sacroiliac joint together, the porous body having:
      a first face configured to contact the sacrum of the sacroiliac joint when the implant is compressed within the sacroiliac joint,
      a second face configured to contact the ilium of the sacroiliac joint when the implant is compressed within the sacroiliac joint, and
      at least one rail projecting outward from one of the first and the second faces and extending from a top edge to a bottom edge of the porous body configured to remove at least one degree of freedom of movement of the implant;
   wherein the pedicle screws and the lateral rod are configured to apply compression to the sacroiliac joint in a direction generally perpendicular to the first face and the second face of the sacroiliac joint implant and maintain the sacroiliac joint in a compressed state and inhibit movement of the implant; and
   wherein the sacroiliac joint implant is unattached to the rod and screws.

2. The sacroiliac joint implant system of claim 1, wherein the porous body comprises porous titanium.

3. The sacroiliac joint implant system of claim 1, wherein the porous body further has a plurality of protrusions configured to promote contact with sacroiliac joint.

4. The sacroiliac joint implant system of claim 3, wherein the protrusions extend from the first face.

5. The sacroiliac joint implant system of claim 3, wherein the protrusions extend from the second face.

6. The sacroiliac joint implant system of claim 1, including a graft window extending between the first and second faces and configured to hold a graft material, wherein the porous body includes a lip surrounding the graft window.

7. The sacroiliac joint implant system of claim 6, wherein the lip is arranged on the first face.

8. The sacroiliac joint implant system of claim 6, wherein the lip is arranged on the second face.

9. The sacroiliac joint implant system of claim 1, wherein the porous body is configured to be placed in the sacroiliac joint through an opening of a guiding tool.

10. The sacroiliac joint implant system of claim 9, wherein the guiding tool includes a box shaped body having an opening extending there through.

11. The sacroiliac joint implant system of claim 9, wherein the guiding tool includes a pair of phalanges configured to anchor the guiding tool to the sacroiliac joint.

12. The sacroiliac joint implant system of claim 1, wherein the sacroiliac joint implant is configured to be placed within the sacroiliac joint via a posterior approach.

13. The sacroiliac joint implant system of claim 1, including a graft window extending between the first and second faces and configured to hold a graft material wherein the graft material is provided in the graft window of the porous body.

14. The sacroiliac joint implant system of claim 13, wherein the graft window is further positioned between a first rail of the at least one rail and a second rail of the at least one rail, wherein the first rail and the second rail extend along a direction that is substantially perpendicular to a longitudinal direction of the porous body.

15. The sacroiliac joint implant system of claim 1, wherein, the sacroiliac joint implant is configured to be placed in the sacroiliac joint after removal of at least a portion of the cortical bone from each of the sacrum and the ilium to expose cancellous bone.

16. The sacroiliac joint implant system of claim 1, wherein the sacroiliac joint implant is configured to be oriented parallel to the sacroiliac joint.

17. The sacroiliac joint implant system of claim 1, wherein the two or more pedicle screws include an iliac screw and either an S-1 screw or an S-2 alar screw, and the lateral rod is secured either between the iliac screw and the S-1 screw or between the iliac screw and the S-2 alar screw.

18. The sacroiliac joint implant system of claim 1, wherein the two or more pedicle screws include an iliac screw, an S-1 screw, and an S-2 alar screw, and the lateral rod is secured between the iliac screw and a long segment rod that is secured between the S-1 screw and the S-2 alar screw.

19. The sacroiliac joint implant system of claim 1, wherein rod is oriented to extend in a direction substantially perpendicular to the first and second face of the implant body.

20. The sacroiliac joint implant system of claim 1, wherein the at least a pair of pedicle screws comprising a first and second screw mounted to a first side of sacroiliac joint and a third screw on an opposite side of the sacroiliac joint, wherein a lateral rod extends between the first and second screw and the rod extending across the sacroiliac joint extends from the third screw and attaches to a location on the lateral rod.

21. The sacroiliac joint implant system of claim 1, wherein the at least one rail includes a first rail projecting outward from the first and second rail projecting outward from the second face.

* * * * *